United States Patent
Ratner et al.

(10) Patent No.: US 7,578,971 B2
(45) Date of Patent: Aug. 25, 2009

(54) RAPID-RESPONSE REVERSIBLE DRY SURFACE $CO_2$ DETECTOR

(75) Inventors: Jeffrey Bruce Ratner, Pinellas Park, FL (US); David Matthew Green, Palm Harbor, FL (US); Darrell Wayne Crick, Athens, WV (US); Marc Edward Halpern, Cherry Hill, NJ (US)

(73) Assignee: Mercury Enterprises, Inc., Clearwater, FL (US)

( * ) Notice: Subject to any disclaimer, the term of this patent is extended or adjusted under 35 U.S.C. 154(b) by 855 days.

(21) Appl. No.: 11/087,299

(22) Filed: Mar. 23, 2005

(65) Prior Publication Data

US 2006/0216828 A1    Sep. 28, 2006

(51) Int. Cl.
 *G01N 31/22*    (2006.01)
(52) U.S. Cl. .............................. 422/56; 422/55; 422/57
(58) Field of Classification Search ........................ None
See application file for complete search history.

(56) References Cited

U.S. PATENT DOCUMENTS

| | | | |
|---|---|---|---|
| 4,728,499 A | | 3/1988 | Fehder |
| 4,954,657 A | * | 9/1990 | Heise et al. ................. 568/584 |
| 4,994,117 A | | 2/1991 | Fehder |
| 5,005,072 A | | 4/1991 | Raemer et al. |
| 5,166,075 A | | 11/1992 | Fehder |
| 5,179,002 A | | 1/1993 | Fehder |
| 5,457,056 A | * | 10/1995 | Dandge et al. .............. 436/166 |
| 6,436,347 B1 | | 8/2002 | Cedeon |
| 6,502,573 B1 | | 1/2003 | Ratner |

OTHER PUBLICATIONS

Zhang et al., "Novel Fixed-Carrier Membranes for CO2 Separation", Journal of Applied Polymer Science, 2002, vol. 86, 2222-2226.*
Mills, Chang, McMurray, Equilibrium Studies on Colorimetric Plastic Film Sensors for Carbon Dioxide, Anal. Chem., 1992, pp. 1383-1389, vol. 64, American Chemical Society.

* cited by examiner

*Primary Examiner*—Yelena G Gakh
(74) *Attorney, Agent, or Firm*—Emanuel Morgenstern

(57) ABSTRACT

Compositions for $CO_2$ detector solutions and rapid-response reversible dry surface $CO_2$ detectors made from them are disclosed. The $CO_2$ detector solutions generally comprise a poly(oxyethylene) based compound, a pH sensitive indicator dye, an organic solvent, a cationic phase transfer agent and an anionic base. However, minimally these detector solutions comprise a poly(oxyethylene) based compound, a pH sensitive indicating dye, an organic solvent and a base. The solutions were embedded onto a solid support made of polyethersulfone filter material in order to form rapid-response reversible dry surface $CO_2$ detectors. Rapid-response reversible dry surface $CO_2$ detectors are produced which function at rates in excess of 180 one-way color changes/minute when exposed to alternating 0% and 5% $CO_2$ concentrations. A preferred embodiment using cationic methyltricaprylylammonium in conjunction with the phenoxide anion is substantially humidity resistant.

9 Claims, No Drawings

RAPID-RESPONSE REVERSIBLE DRY SURFACE $CO_2$ DETECTOR

BACKGROUND OF THE INVENTION (1) Field of Invention

This invention relates to dry surface $CO_2$ detectors. More specifically it relates to rapid-response reversible dry surface $CO_2$ detectors prepared from a solution comprising a poly (oxyethylene) based compound, a pH sensitive color indicator dye, an organic solvent, a cationic phase transfer agent, and an anionic base.

(2) Description of Prior Art

Dry surface $CO_2$ detectors are known in the prior art. They have numerous applications including uses in industrial monitoring, environmental monitoring and in medicine.[1] Accurate detection of particular threshold concentrations of $CO_2$ in gaseous samples can be of critical importance in the medical field, particularly when attempting to confirm the proper placement of an endotracheal tube in the airway of a patient. An appropriate properly calibrated $CO_2$ detector which can be inserted into the air path allows one to distinguish between an endotracheal tube placed properly into the airway, through which respiratory concentrations of expired $CO_2$ will be detected, and a tube improperly placed into the esophagus through which no expired $CO_2$ will normally be detected. The difference between a properly and improperly placed endotracheal tube can very quickly become a life or death matter and so the ability to quickly, easily, safely and accurately distinguish between the relevant concentrations of $CO_2$ is highly desirable.

The dry surface $CO_2$ detector provides a great advantage over previous technologies such as the Einstein $CO_2$ detector because the Einstein $CO_2$ detector utilizes a liquid $CO_2$ detecting solution, and is therefore far less versatile and can even present certain hazards when improperly used. When appropriate safe chemistry is used, the dry surface $CO_2$ detector can be readily be placed into the air path in any of a number of configurations without any concern that the patient will aspirate any harmful $CO_2$ detecting materials. The dry surface detector may be placed for example, either inside the endotracheal tube, inside an extension of the endotracheal tube, into a resuscitator bag assembly, or into a specially designed holder which is designed to connect into the air path of the patient such as the single patient use carbon dioxide detector as described in U.S. Pat. No. 6,502,573, herein incorporated by reference.

Further, a rapid-response reversible dry surface $CO_2$ detector which will repeatedly not only rapidly indicate the presence of respiratory concentrations of $CO_2$ (4.5%-5%) but which will also rapidly indicate the change back to ambient $CO_2$ concentration (~0.03%) is even more desirable than a single response detector for endotracheal intubation purposes. Such a rapid-response reversible detector can not only confirm initial proper placement of the endotracheal tube but can also confirm continued proper placement of the tube. With each exhalation, respiratory concentrations of $CO_2$ will be exhaled through a properly placed tube while with each inhalation, ambient concentrations of $CO_2$ will be inhaled through the properly placed tube. With a detector that will repeatedly indicate the change from ambient to respiratory concentrations of $CO_2$ and back again, it becomes possible to verify breath by breath that the patient is continuing to breathe properly through the tube.

Another important point is that using the method of checking for increased concentrations of expired $CO_2$ through an intubation tube as a means of verifying correct tube placement can result in a rare false positive initial test for proper intubation. This may occur when there is increased $CO_2$ concentration present in the esophagus due to, for example, recent consumption of carbonated beverages, which may lead to $CO_2$ being expelled through an intubation tube that has been improperly inserted into the esophagus, thus giving a false positive initial indication regarding the success of the intubation. In such a situation a rapid-response reversible detector that continuously responds to both the upward and downward changes in $CO_2$ concentration in the air path would quickly subsequently reveal when tube placement is improper. However, in this unusual situation, a single-response non-reversible detector would only indicate the initial false positive (high concentration of $CO_2$ present) for correct intubation but would not give any further information, thus likely quickly leading to a very dangerous situation.

To effectively serve the function of assisting in verifying proper initial placement of an endotracheal tube, the detector must respond to the relevant changes in $CO_2$ concentration within an appropriate respiratory timeframe, meaning no more than 20 seconds at the slowest (See U.S. Pat. No. 5,166,075). So non-reversible detectors designed to give a one-time response indicating the presence or absence of $CO_2$ could function successfully for the intended purpose even when they respond relatively slowly.

To serve the function of verifying continued proper placement of an endotracheal tube, a $CO_2$ detector must respond to the relevant changes in $CO_2$ concentration within a shorter timeframe. Assuming a respiratory rate of 15 breaths/minute for a healthy adult (see U.S. Pat. No. 6,436,347), such an application requires that clear indications of the relevant changes in $CO_2$ concentration be given by the detector within 2 seconds of exposure to a changed concentration of $CO_2$ in order to observe breath-by-breath changes clearly. However sick or stressed adults may have a faster respiration rate. Children have an average respiration rate of 20 to 40 breaths/minute and newborns have an average respiration rate of 30 to 60 breaths/minute. And of course, a faster respiratory rate would shorten the acceptable detector response time (0.75 to 1.5 seconds for children, 0.5 to 1.0 seconds for newborns). Therefore a reversible $CO_2$ detector with a one-way response time faster than 0.5 seconds is preferable so as to provide the necessary function in virtually any medical situation that might be encountered.

U.S. Pat. No. 5,005,572 describes the production of dry surface $CO_2$ detectors employing a color indicator dye and a phase transport enhancer. Several examples are given of functional $CO_2$ detectors which will change color so as to indicate the presence of a given concentration of $CO_2$ in a gaseous sample. These detectors incorporate a phase transport enhancer into their composition. A broad range of possible phase transport enhancers is claimed, anything of the form:

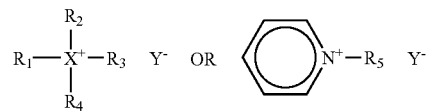

where

X=N or P;

$R_1$, $R_2$, $R_3$ and $R_4$ are selected from the group consisting of $C_1$-$C_{12}$ alkyl, $C_1$-$C_4$ substituted alkyl wherein the substituent is a $C_1$-$C_4$ alkyl or phenyl group, naphthyl, benzyl, and pyridine;

$R_5$ is selected from the group consisting of $C_1$-$C_{12}$ alkyl or benzyl; and Y⁻ is an anion selected from the group consisting of hydroxide, fluoride, chloride, bromide, iodide, carbonate and tetrafluoroborate.

In U.S. Pat. No. 5,005,572, only a few examples are given of reversible $CO_2$ detectors which will not only change color in response to the presence of respiratory concentrations of $CO_2$ (4.5-5%) but which will also substantially revert back to their initial color when subsequently exposed to a lower ambient concentration of $CO_2$ (~0.03%). The particular examples given all utilize a combination of TBAH (tetrabutylammonium hydroxide) as a phase transport 'enhancer' in combination with one of several pH sensitive indicating dyes in their formulations. However, no specific time frames for response of the 'rapid' detectors are given which would allow evaluation of the suitability of these particular detector compositions for the purpose of monitoring ongoing respiration and/or monitoring continued correct placement of an endotracheal tube.

U.S. Pat. Nos. 4,728,499; 4,994,117; 5,166,075; and 5,179,002 disclose examples of $CO_2$ detectors produced by drying an indicating solution onto a carrier. The indicating solution is aqueous and/or non-volatile and is comprised of a basic solution, a pH sensitive indicator dye, and a high boiling, water miscible hygroscopic liquid but does not make use of phase transport enhancers. Workable $CO_2$ detectors are disclosed but among these patents, only one example, given both in U.S. Pat. No. 5,166,075 and in U.S. Pat. No. 5,179,002, provides for a reversible detector which will indicate the change from ambient to respiratory concentrations of $CO_2$ as well as the change back to ambient $CO_2$ concentrations. This example utilizes a combination of water, sodium carbonate, glycerol and m-cresol purple. Upon exposure to 5% $CO_2$, a detector made according to this example will give a color-change response in 5 seconds and will turn back to its original color quickly upon re-exposure to ambient $CO_2$ concentrations. These response times may be fast enough to be useful in verifying initial correct placement of an endotracheal tube but will not be fast enough to be reliable for determining continued correct placement of an endotracheal tube which may require response and reverse-response times to each be on the order of 2 seconds or less.

U.S. Pat. No. 6,436,347 describes the use of quaternary ammonium and quaternary phosphonium phase transport enhancers to produce fast response calorimetric indicators which are substantially insensitive to humidity. Specific examples are given using the specific phase transport enhancers tetraoctylammonium hydroxide, trimethylhexadecylammonium hydroxide, and tetradecyltrihexylammonium hydroxide together with Thymol blue to produce functional $CO_2$ detectors. However, beyond a single mention of the word 'reversible' in column 1 of the 'Background of the Invention' section, no evidence is given of a reverse-response by the detector when the higher $CO_2$ concentration gaseous sample (5% $CO_2$) is subsequently replaced with ambient air (0.03% $CO_2$). Without an equally swift reverse-response when $CO_2$ concentrations return to ambient levels of 0.03%, these fast response detectors would not be suitable to accomplish the continued monitoring of correct placement of an endotracheal tube.

Though the examples given in U.S. Pat. No. 6,436,347 utilize only tetraoctylammonium, trimethylhexadecylammonium, or tetradecyltrihexylammonium cations, coupled with a hydroxide anion, the claims are much broader including any phase transport enhancers of the form:

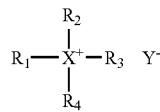

where X is a nitrogen or phosphorus atom; and where $R_1$, $R_2$, $R_3$, and $R_4$ are alkyl groups and at least one of the alkyl groups has at least 13 carbons, and at least one of the other alkyls have 6 to 8 carbons, and the remaining alkyls (if any) have 1 to 12 carbons;

Y⁻ is an anion selected from the group consisting of hydroxide, fluoride, chloride, bromide, iodide, carbonate and tetrafluoroborate.

SUMMARY OF THE INVENTION

Numerous chemical combinations were explored in an attempt to find improved and/or alternative chemistry to be used in production of reliable, rapid-response, reversible dry surface $CO_2$ detectors. The present invention is a group of related formulas for $CO_2$ detecting solutions and the rapid-response reversible dry surface $CO_2$ detectors that can be made from them. The $CO_2$ detector solutions of the present invention generally comprise a poly(oxyethylene) based compound, a pH sensitive indicator dye, an organic solvent, a cationic phase transfer agent and an anionic base. Some success was also achieved in formulating $CO_2$ detector solutions which comprised a poly(oxyethylene) based compound, a pH sensitive indicator dye, an organic solvent, and a base and no phase transfer agent yet which still produced functioning rapid-response, reversible dry surface $CO_2$ detectors. Polyethersulfone strips or disks were used as the solid support onto which the detector solutions were embedded to form solid dry surface detectors. Generally the phase transfer agents utilized consisted of cationic quaternary ammonium compounds and cationic crown ether/alkali metal complexes. These were utilized in combination with a variety of anionic bases including hydroxide, methoxide, tert-butoxide, phenoxide and oxyphosphorous anions. Further, the successes achieved lead to theoretical expectations for some broader classes of ingredients.

These rapid-response reversible dry surface $CO_2$ detectors exhibit rapid color change response when exposed to normal respiratory concentrations of $CO_2$ (4.5%-5%) as well as rapid reverse-response (substantial return to original color) upon subsequent re-exposure to ambient $CO_2$ (~0.03%) concentrations. Many of the $CO_2$ detector formulations discovered respond quite rapidly, functioning at a rate in excess of 180 one-way color changes/minute (i.e. 90 back-and-forth color change cycles/min.). This is significantly faster than what is described for any of the reversible dry surface $CO_2$ detectors disclosed in U.S. Pat. Nos. 5,005,572; 5,166,075; 5,179,002; or 6,436,347; referred to above.

The detectors of the present invention do not lose their ability to respond to changes in $CO_2$ concentrations after their initial responses but rather substantially repeat both the initial and reverse color changes in an ongoing manner in response to exposure to continued changes in $CO_2$ concentration. Depending upon the environmental conditions to which they are exposed, some of the compositions disclosed will produce detectors which continue to function in this manner for a long period of time without losing the rapid response and reverse-response characteristics while others only function for a shorter period. Depending upon the particular embodiment chosen, the length of functionality may be dependent upon exposure to humidity, extreme temperatures or other environmental factors.

For the great majority of successful formulations examined, both the initial and reverse-response times are well within the 2-second time frame necessary to allow a detector to effectively monitor respiration at rates of up to 15 breaths/minute. In most cases the detectors will respond to relevant changes in $CO_2$ concentration in 0.33 second or less, allowing ongoing monitoring of respiration at rates up to at least 90 breaths/minute. This offers an appropriate range for the purposes of both determining correct initial placement of an endotracheal tube as well as to continuously monitor that placement of the endotracheal tube remains correct once inserted in any situation likely to be encountered.

Further, a preferred embodiment of a rapid-response reversible dry surface $CO_2$ detector made from a solution comprising a cationic methyltricaprylylammonium phase transfer agent in conjunction with the phenoxide anion shows excellent resistance to humidity; its speed of color change, its intensity of color change and its longevity of function not being significantly affected by high humidity levels.

DETAILED DESCRIPTION OF THE INVENTION

The primary general composition of the solutions utilized for creating rapid response reversible dry surface $CO_2$ detectors comprised a poly(oxyethylene) based compound, a pH sensitive color indicator, an organic solvent, a cationic phase transfer agent and an anionic base. However, it was discovered that functional reversible dry surface $CO_2$ detectors could also be prepared from solutions which contained only a poly(oxyethylene) based compound, a pH sensitive color indicator, an organic solvent and a base. Several examples of this latter class of detectors are given in the 'Examples' section below though the bulk of exploration was done using compositions that included a cationic phase transfer agent and an associated anionic base as part of the formulation.

All the various potential $CO_2$ detecting solutions tested were embedded onto a solid support in order to create potential rapid-response reversible dry surface $CO_2$ detectors. In all experiments described below, the solid support used was made of a polyethersulfone filter material. Supor® polyethersulfone filter disks (and strips cut from them) manufactured by Pall Corporation, with pore sizes of 0.2 μm or 0.45 μm, were dipped in or smeared with potential $CO_2$ detector solution and allowed to dry. The 0.45 μm pore size Supor® material was generally found to be preferable with the detecting solution applied to the matte side only. Although all experimentation described below was done with these polyethersulfone disks and strips, embodiments of the present invention can certainly be created utilizing other suitable materials as the solid support. Functioning detectors were also created using Kimwipes®, Whatman #1 filter paper and teflon filter media. (See also, for example, U.S. Pat. No. 5,005,072). However compatibility issues must be kept in mind when choosing support material as, for example, chlorinated hydrocarbon solvents are not compatible with the Supor® polyethersulfone filter material. The present invention is not meant to be limited to the use of polyethersulfone filter material as a solid support for the dry surface detector.

In accord with the general detector solution compositions outlined above, many different specific potential formulations which might yield functional rapid-response reversible dry surface $CO_2$ detectors were tested. Ingredients and relative amounts of ingredients, as well as experimental methods for combining said ingredients were all varied in attempts to find new rapid response reversible dry surface $CO_2$ detector compositions. Poly(oxyethylene) based compounds, pH sensitive color indicator dyes, solvents, phase transfer agents and bases were all varied in attempts to find optimal compositions. And many successful combinations were discovered, some more suited than others for the originally intended purpose of creating rapid-response reversible dry surface $CO_2$ detectors for use in an esophageal breathing system to monitor respiration.

Research into the ultimate suitability of the various embodiments of the present invention for the originally intended application in terms of shelf life, temperature resistance, safety of the chemicals included in the various compositions, optimal storage means, etc. is ongoing. It is worth noting that a chemical composition that might be toxic when inhaled, can still be made safe for the intended application by preventing the possibility of inhalation. This might be accomplished in a number of ways. For example, by affixing such toxic chemicals to the detector support in such a way that they cannot escape the fixture. An air filter placed in the air path between the detector and the patient as, for example, in U.S. Pat. No. 6,502,573, can also be useful to prevent harmful materials from being inhaled. Or, as another possibility, inhalation of potentially dangerous chemicals could be prevented by limiting inclusion of potentially dangerous compositions to one-way apparatuses where only the patient's exhalation makes contact with the detector.

The $CO_2$ detecting solutions and the reversible rapid-response dry surface $CO_2$ detectors of the present invention make use of a pH sensitive color indicator dye. The key reactions that bring about the color changes of a pH sensitive color indicating dye are the protonation of the anionic indicating dye ($D^-$) and the deprotonation of the neutral protonated indicating dye (DH):

1)

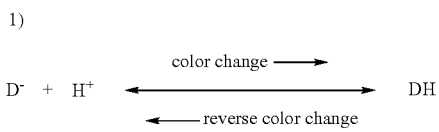

In a $CO_2$ detector which utilizes a pH sensitive dye as above, $CO_2$ molecules react with $H_2O$ molecules via the reaction:

$$H_2O + CO_2 \leftrightarrows H_2CO_3 \qquad 2)$$

Then:

$$H_2CO_3 \leftrightarrows H^+ + HCO_3^- \qquad 3)$$

and further:

$$HCO_3^- \leftrightarrows H^+ + CO_3^{2-} \qquad 4)$$

The forward reactions 2) through 4) make protons available for protonation of the indicating dye, thereby affecting the equilibrium of the system such that reaction 1) proceeds forward and the indicator manifests a color change. The reverse reactions 4) through 2) utilize protons thus affecting the equilibrium of the system such that reaction 1) proceeds in reverse thereby manifesting the reverse color change.

Various aspects of the theoretical basis for the functioning of dry surface $CO_2$ detectors which make use of a pH sensitive dye to give a calorimetric response upon exposure to various $CO_2$ concentrations has been given previously in U.S. Pat. Nos. 4,728,499; 4,994,117; 5,005,572; 5,166,975; 5,179,002;

and 6,436,347; as well as in scientific papers such as one entitled 'Equilibrium Studies on Colorimetric Plastic Film Sensors for Carbon Dioxide' written by Mills, Chang, and McMurray and published in *Anal. Chem.* 1992, 64, 1383-1389.

$H_2O$ must be present in sufficient quantities to ultimately allow the forward reactions 2)-4) to occur when $CO_2$ is present or else the pH sensitive dye incorporated into the $CO_2$ detector could not function in this manner. But, in the case of many embodiments of the present invention, only a tiny amount of $H_2O$ is required for functionality and such $H_2O$ can come from ambient humidity, respiratory humidity, or may be incorporated into the formulation of the detector itself. As such, the $CO_2$ detection solutions from which the present dry surface $CO_2$ detectors are produced need not be aqueous. Success has been achieved utilizing wholly non-aqueous formulations in organic solvents as well as formulations that incorporate tiny amounts of $H_2O$ or somewhat larger quantities of $H_2O$.

A number of different poly(oxyethylene) based compounds were utilized in the various compositions of $CO_2$ detection solutions tested. The most commonly used were Triton X-15 Octylphenol ethoxylate supplied by Sigma Aldrich, and TDA-15 polyoxyethylene (15) tridecyl alcohol supplied by Chemax, two water insoluble ethoxylated alcohols. But experiments were also performed with: TDA-3 polyoxyethylene (3) tridecyl alcohol supplied by Chemax, Triton X-100 Octylphenol ethoxylate supplied by Sigma Aldrich, Triton RW-20 Alkylamine Ethoxylate supplied by Dow Chemical, 2EH-5 Polyoxyethylene (5) 2 ethyl hexanol supplied by Chemax, Brij 78 polyoxyethylene 21 stearyl ether supplied by Sigma Aldrich, LA-4 polyoxyethylene (4) lauryl alcohol supplied by Chemax, CSA-3 polyoxyethylene (3) cetyl stearyl alcohol supplied by Chemax, polyethylene glycol 400 supplied by Sigma Aldrich, polyethylene glycol 8000 supplied by Sigma Aldrich, and TDA-1 Tris[2-(2-methoxyethoxy)ethyl]amine supplied by Sigma Aldrich.

Functional detectors were created utilizing each of these substances with the exception of TDA-1 Tris[2-(2-methoxyethoxy)ethyl]amine. Though experimentation was only carried out with the limited group of poly(oxyethylene) based compounds listed above, many other poly(oxyethylene) based compounds could potentially be utilized in the production of functional rapid-response reversible dry surface $CO_2$ detectors. The invention is not meant to be limited to the group of poly(oxyethylene) based compounds listed above.

It is also worth noting that many poly(oxyethylene) based compounds are hygroscopic and so, in addition to serving to bind the $CO_2$ detecting composition to the solid support to make the dry surface detector, they also attract/hold water and so may assist in the process of providing the water necessary to the chemical reactions which bring about the color change of the pH sensitive color indicator on the $CO_2$ detector.

The primary pH sensitive indicating dyes chosen for experimentation were Thymol blue and m-cresol purple (though some experiments were attempted with Bromthymol blue and phenolphthalein as well). Many different successful $CO_2$ detector compositions were created using either Thymol blue or m-cresol purple. However the invention is not meant to be limited to the use of these 2 particular indicators. A large variety of pH sensitive indicator dyes are currently available, each with their own particular characteristics. For example: phenol red, bromocresol purple, rosolic acid, cresol red, m-nitrophenol, xylenol blue, curcumin, cresolphthalein, thymolphthalein, malachite green, N,N-dimethylaniline, and bromcresol green. (See Table 3 of U.S. Pat. No. 5,005,572) A number of the many indicators available may be suitable for creating other embodiments of the present invention. Further, depending upon the particular detector performance characteristics desired including the particular $CO_2$ concentrations to be distinguished, other indicators may be more suitable than those chosen for the experimentation described herein.

The organic solvent used in almost all cases was methanol. However some experiments which produced functional detectors were performed using ethanol, t-butanol, dichloromethane, toluene or a mixture of methanol and ethanol. $CCl_4$ was also used unsuccessfully. Other organic solvents other than those tested could certainly be utilized to create functional reversible dry surface $CO_2$ detectors as well and so the present invention is not meant to be limited to methanol as a solvent. However, when manufacturing rapid-response reversible dry surface $CO_2$ detectors for the intended purpose of monitoring respiration, many of the other available functional solvents may not, for one reason or another, function safely and effectively for this intended purpose and so might not be suitable for practical use.

Numerous cationic phase transfer agents in conjunction with various anionic bases were tested in the attempts to create functioning rapid-response reversible dry surface $CO_2$ detectors. The cationic phase transfer agents tested primarily broke down into 2 categories, quaternary ammonium and crown ether/metal complexes. Of the quaternary ammonium phase transfer agents, success was had with methyltributyl, tetrabutyl, methyltricaprylyl (not to be confused with 'methyltricapryl' which is another name for methyltrioctyl) and tetraoctyl. The present invention is not meant to be limited to the few representative species of quaternary ammonium tested. It is anticipated that similar success can be readily achieved with a large variety of quaternary ammoniums and quaternary phosphoniums with alkyl or substituted alkyl chains of anywhere between 1 and 24 carbons.

It should be mentioned that U.S. Pat. No. 6,436,347 argues in describing an invention with certain similarities to the present invention, that if all 4 alkyl chains of a quaternary ammonium or phosphonium phase transfer agent are longer than "10-12 carbon atoms, the amount of water present will be insufficient for the color changing reaction to take place properly, even when the air contacting the indicator composition is humid." And there may be some similar limitation found to be applicable to the present invention upon further investigation. However, U.S. Pat. No. 6,436,347 also claims that "if the indicator composition is too hydrophilic, because the number of carbon atoms of the carbon chains is much smaller than 8 and/or because the indicator composition includes a strongly hydrophilic substance, the indicator composition will respond very slowly to carbon dioxide." But in the experimentation leading to the present invention, methyltributylammonium and tetrabutylammonium were both successfully utilized, and $CO_2$ detector compositions utilizing these two phase transfer agents responded almost as quickly as those with three 8-10 carbon chains. So the lower limitations for lengths of carbon chains discussed in U.S. Pat. No. 6,436,347 are apparently not applicable to the present invention. Similarly, particularly in light of this observed difference between the limitations of the present invention as compared to that described in U.S. Pat. No. 6,436,347, it should not be assumed that the upper limits of carbon chain lengths suggested in U.S. Pat. No. 6,436,347 apply to the present invention either.

Of the cationic crown ether/metal complexes, success was achieved with crown ether/alkali metal complexes but not with crown ether/alkaline earth metal complexes. Functional rapid-response reversible dry surface $CO_2$ detectors were produced utilizing:

18-crown-6 ether/sodium complex,
18-crown-6 ether/potassium complex,
dibenzo 18-crown-6 ether/sodium complex,
dibenzo 18-crown-6 ether/potassium complex,
and di(tert-butyl)dibenzo 18-crown-6 ether/potassium complex.

Whereas attempts to utilize dibenzo 18-crown-6 ether in conjunction with barium and dibenzo 15-crown-5 ether in conjunction with calcium did not produce functional detectors using our formulations. It is anticipated that other crown ether/alkali metal complexes or other macrocyclic polyether/alkali metal complexes will function similarly to those we have tested and the invention is not meant to be limited to just those few crown ether/alkali metal complexes mentioned above.

The basic anions that were successfully utilized in conjunction with the above-mentioned cationic phase transfer agents were hydroxide, methoxide, t-butoxide, phenoxide, and a mixture of phosphate, hydrogen phosphate and di-hydrogen phosphate. Functioning rapid-response reversible dry surface $CO_2$ detectors were produced utilizing each of the following combinations of cationic phase transfer agents and anionic bases:

Methyltricaprylylammonium in conjunction with methoxide, phenoxide, or a mixture of phosphate, hydrogen phosphate and di-hydrogen phosphate;
18-crown-6 ether/sodium complex, dibenzo 18-crown-6 ether/sodium complex, methyltributylammonium, or tetrabutylammonium in conjunction with the methoxide anion;
18-crown-6 ether/potassium complex, dibenzo 18-crown-6 ether/potassium complex, dibenzo 18-crown-6 ether/sodium complex, or di(tert-butyl)dibenzo 18-crown-6 ether/potassium complex in conjunction with the hydroxide anion;
Dibenzo 18-crown-6 ether/potassium complex or di(tert-butyl)dibenzo 18-crown-6 ether/potassium complex in conjunction with the tert-butoxide anion.

The present invention is not meant to be limited to just those basic anions listed above. It is anticipated that other alkoxides, substituted alkoxides, substituted phenoxides, and oxyphosphorous anions could be successfully employed as basic anions in conjunction with cationic phase transfer agents as delineated above in order to produce functional rapid-response reversible dry surface $CO_2$ detectors.

Though the above representations appear to us to be theoretically correct, it is also possible to view the majority of the $CO_2$ detector solution compositions we employed as combinations of a poly(oxyethylene) based compound, a pH sensitive color indicator dye, an organic solvent, and a neutral phase transfer agent with or without an additional base. When viewed from this perspective, the successful combinations that led to functional rapid response reversible dry surface $CO_2$ detectors would be characterized differently. One could then say that successful $CO_2$ detectors were produced using a poly(oxyethylene) based compound, a pH sensitive indicating dye, an organic solvent and one of the following:
tetrabutylammonium hydrogen sulfate and sodium methoxide;
methyltributylammonium hydrogen sulfate and sodium methoxide;
methyltricaprylylammonium hydrogen sulfate and sodium methoxide;
methyltricaprylylammonium hydrogen sulfate and sodium phenoxide trihydrate;
a mixture of methyltricaprylylammonium phosphate, methyltricaprylylammonium hydrogen phosphate, and methyltricaprylylammonium dihydrogen phosphate;
methyltricaprylylammonium phenoxide;
tetraoctyl ammonium phenoxide;
18-crown-6 ether, water, and potassium hydroxide;
18-crown-6 ether and sodium methoxide;
dibenzo-18-crown-6 ether and potassium hydroxide;
dibenzo-18-crown-6 ether, water, and potassium hydroxide;
dibenzo-18-crown-6 ether and sodium methoxide
dibenzo-18-crown-6 ether and potassium tert-butoxide;
di(tert-butyl)dibenzo-18-crown-6 ether, water, and potassium hydroxide;
di(tert-butyl)dibenzo-18-crown-6 ether and potassium tert-butoxide;

However the invention is not meant to be limited to these phase transfer agents. From this perspective, it is anticipated that other quaternary ammonium alkoxides, quaternary ammonium phenoxides, quaternary ammonium phosphorus oxyanions, quaternary ammonium hydrogen sulfates, quaternary phosphonium alkoxides, quaternary phosphonium phenoxides, quaternary phosphonium phosphorus oxyanions, and macrocyclic polyethers could function successfully as phase transfer agents in rapid-response reversible dry surface $CO_2$ detectors.

In the cases where pH adjustment was necessary in preparing the detector solutions, it was generally attempted to adjust the pH of the solution to be just slightly above the point where the anionic form of the pH sensitive indicator dye becomes protonated. When this condition is met, then the small amount of carbonic acid formed from exhaled $CO_2$ reacting with $H_2O$ and interacting with the detector will be enough to lower the pH to a point where a visible, often dramatic, color change takes place.

Most of the successful rapid-response reversible dry surface $CO_2$ detectors created using Thymol Blue behaved similarly in terms of degree of color change vs. % $CO_2$. Most of these detectors were blue at 0% $CO_2$ As the $CO_2$ concentration increased to 1%, they changed to blue-green, at 2% to green, at 3% to green-yellow (more green than yellow), at 4% to yellow-green (more yellow than green) and at 5% to yellow. Those successful rapid-response reversible dry surface $CO_2$ detectors that were formulated with m-cresol purple generally behaved similarly, gradually changing from (for example) purple to yellow, as the $CO_2$ concentration increased from 0% to 5%.

These color change vs. $CO_2$ concentration responses are quite suitable for use in an esophageal breathing system to monitor respiration. Since the $CO_2$ concentration in exhaled breath is normally on the order of 4.5% to 5% and ambient $CO_2$ concentration is normally on the order of 0.03%, a very dramatic color change is visible on these detectors as they are alternately exposed to ambient air and exhaled breath. Further these detectors are sensitive enough to exhibit easily visually appreciable color change when the $CO_2$ concentration changes from ambient concentration to as low as about 1-2% allowing them to still be useable in situations where abnormal respiration is occurring and the $CO_2$ concentration of the exhaled breath is lower than normal. Further, the graded color change vs. $CO_2$ concentration effect that occurs, when properly calibrated, can offer not only qualitative evidence that $CO_2$ is being exhaled but also quantitative information about how much $CO_2$ is present in the exhalation.

An overall color change scale was created for the purposes of comparing the functionality of the various $CO_2$ detector formulations. The overall color change scale ranges from 1 to 10 where 1 is a non-functional detector and 10 is an ideal very rapidly functioning $CO_2$ detector with vivid indicating colors and great contrast between indicating colors. The overall color change rating takes into account 3 factors: change of hue, change of luminosity and speed of color change. Glidden paint color cards and the Microsoft® Paint program were used for color comparison.

All of the more successful (those rated 7 or higher on a scale of 1-10 for overall color change) rapid-response reversible dry surface $CO_2$ detectors created were capable of functioning at a rate of 180 readily visible one-way color changes/ minute or faster. This equates to a color change speed of 0.33 seconds or faster. This would allow them to keep up with a respiration rate of 90 breaths/minute or faster depending upon the particular formulation. This rapid response is highly suitable for the intended purpose of monitoring respiration which normally is on the order of 15 breaths or less/minute but which can be significantly faster when dealing with children, infants or in certain extreme situations as mentioned above.

Another important factor to consider when determining the applicability of a particular $CO_2$ detector formulation to the specific purpose of monitoring respiration is humidity resistance. Because exhaled air contains 100% humidity under normal circumstances and ambient air has varying degrees of humidity that can also reach nearly 100%, a $CO_2$ detector must have some degree of humidity resistance in order to fulfill the purpose of monitoring respiration in an ongoing manner. Otherwise upon exposure to ambient air when removed from a wrapper or the like, or upon being breathed upon, the $CO_2$ detector could fail and become useless. It is not necessary that the detector be completely humidity resistant but it must be able to function long enough to fulfill its desired purpose. Previous patents that have dealt with $CO_2$ detectors for the purpose of monitoring respiration have deemed 10 to 20 minutes of continued functioning to be a suitable time to accomplish the purpose of monitoring ongoing respiration for most practical purposes (See U.S. Pat. No. 5,166,075). Of course a detector with a low humidity resistance (and short functional life) could still be suitable for use in a device designed to make a one-time-only test for the presence of $CO_2$.

A preferred embodiment of the present invention utilizing a cationic methyltricaprylylammonium paired with a phenoxide anion has shown excellent resistance to humidity and can even be washed with water and then dried without affecting its performance or composition. Formulations of rapid-response reversible dry surface $CO_2$ detectors using these components were shown to function for over 24 hours at 100% humidity, more than enough time for virtually any desired respiratory monitoring application. Similarly a cationic tetraoctylammonium paired with a phenoxide anion has also shown this high level of humidity resistance though the overall functioning of the formula prepared with methyltricaprylylammonium is preferred, offering a more dramatic color change. Most of the other formulations utilized do not show such a high level of humidity resistance although many offer enough humidity resistance to potentially be useful for the intended purpose of monitoring respiration in an ongoing manner.

Shelf life is also an important factor in determining the suitability of various embodiments of the present invention for the purpose of monitoring respiration. A $CO_2$ detector to be used in medical situations must be available immediately when necessary and so must be able to last in some stored form for a period of months or years until that need arises. It is also preferable that it be able to withstand certain changes in environmental factors, particularly changes in temperature that may occur during the storage period. Although no extensive testing has been done as yet to determine the best methods for storing the various formulated $CO_2$ detectors or to determine how long which detectors will last under what conditions, one embodiment using a cationic methyltricaprylylammonium in conjunction with a methoxide anion was shown to function at a rate in excess of 180 one-way changes/ minute after being stored for a year (See example #7 below).

Although the main objective in investigating the various formulations tested was to produce excellent rapid-response reversible dry surface $CO_2$ detectors for use in the process of determining initial and ongoing correct placement of an inserted endotracheal tube and to monitor that respiration is occurring properly in an ongoing manner, the invention is not meant to be limited to such uses. Rapid-response reversible dry surface $CO_2$ detectors potentially have application in many areas as mentioned previously and the present invention will, in time, likely show itself to be well suited to other applications where $CO_2$ detectors are required or desired.

EXAMPLES

The materials used in the following examples were:
Brij 78 polyoxyethylene 21 stearyl ether supplied by Sigma Aldrich
TDA-1 Tris[2-(2-methoxyethoxy)ethyl]amine supplied by Sigma Aldrich
TDA-3-polyoxyethylene (3) tridecyl alcohol supplied by Chemax
TDA-15 polyoxyethylene (15) tridecyl alcohol supplied by Chemax
2EH-5-Polyoxyethylene (5) 2 ethyl hexanol supplied by Chemax
LA-4-polyoxyethylene (4) lauryl alcohol supplied by Chemax
CSA-3-polyoxyethylene (3) cetyl stearyl alcohol supplied by Chemax
RW-20 Alkylamine Ethoxylate supplied by Dow Chemical
Triton X-15 Octylphenol ethoxylate supplied by Sigma Aldrich
Triton X-100 Octylphenol ethoxylate supplied by Sigma Aldrich
Polyethylene glycol 400 supplied by Sigma Aldrich
Polyethylene glycol 8000 supplied by Sigma Aldrich
m-cresol purple, sodium salt supplied by Spectrum
m-cresol purple, sodium salt supplied by Sigma Aldrich
Thymol Blue supplied by Sigma Aldrich
Thymol blue free acid supplied by Acros
Thymol blue sodium salt supplied by Acros
methanol (supplied by Sigma Aldrich and HPLC grade from EM Science among others)
ethanol, 200 proof supplied by Sigma Aldrich
dichloromethane supplied by Fisher
toluene supplied by Sigma Aldrich
toluene supplied by EM Science
potassium hydroxide supplied by Fisher
potassium hydroxide (85%) supplied by JT Baker
potassium tert-butoxide supplied by Sigma Aldrich
sodium methoxide supplied by Sigma Aldrich
25 wt % sodium methoxide in methanol supplied by Sigma Aldrich
30 wt % sodium methoxide in methanol supplied by Sigma Aldrich
sodium phenoxide trihydrate supplied by Sigma Aldrich
trisodium phosphate supplied by Sigma Aldrich
HPLC grade hexane supplied by Acros
distilled water supplied by various sources
tetrabutylammonium hydrogen sulfate supplied by Dishman methyltributylammonium hydrogen sulfate supplied by Sachem methyltricaprylylammonium hydrogen sulfate (Aliquat® 128 HS aka Aliquat® 134HS) supplied by Cognis methyltricaprylylammonium chloride supplied by Sigma Aldrich tetraoctylammonium hydrogen sulfate supplied by Fluka 18-crown-6 ether supplied by Eskay Industries dibenzo-18-crown-6 ether supplied by Sigma Aldrich dibenzo-18-crown-6 ether (Aliplex® 186) supplied by Cognis di(tert-butyl)dibenzo-18-crown-6 ether supplied by Sigma Aldrich Supor® polyethersulfone filter strips and discs manufactured by Pall Corporation Whatman #1 filter cup Glidden paint color cards and the Microsoft® Paint program were used for color comparison.

Example 1

1 g Triton X-15 Octylphenol ethoxylate, was combined with 0.15 g $KOC(CH_3)_3$, 0.01 g Thymol Blue (supplied by Acros), and 50 ml ethanol. The mixture was heated to a boil. The solvent was then removed by boiling off to obtain a total volume between 5 and 10 ml. Using a cotton ball, the resulting solution was applied to the surface of a Supor® polyethersulfone filter strip and air-dried. The result was a solid, $CO_2$ detector which changed from blue to yellow upon exposure to 5% $CO_2$ concentration and reverted to blue upon re-exposure to ambient (~0.03%) $CO_2$ concentrations (i.e. a reversible $CO_2$ detector). During the peak of functionality, the overall color change, based on change of hue, change of luminosity and speed of color change, was moderate (rated 7 on a scale of 1 to 10). The rate of substantially complete change of color was on the order of 180 one-way changes/minute (i.e. 90 back and forth cycles/minute). The detector was not highly humidity resistant, remaining functional for less than an hour at 100% humidity, gradually becoming non-functional within that time. When exposed to water, the dye washed off the detector.

Based on a 10 ml solution, the detector solution composition by weight %:

Thymol Blue Free Acid: 0.1%

Triton X-15 Octylphenol ethoxylate: 10%

$KOC(CH_3)_3$: 1.5%

Ethanol: 88.4%

Example 2

A formulation was prepared using Polyethylene glycol 400, Thymol blue (supplied by Sigma Aldrich) and methanol. The solution was pH adjusted with 0.1 M aqueous KOH (supplied by JT Baker) until a blue solution was obtained. A polyethersulfone filter strip dipped in the solution and then dried resulted in a sample which showed a very rapid reversible color change to yellow upon exposure to 5% $CO_2$. However, after sitting overnight, the sample was non-functional and a freshly prepared sample showed decreasing activity throughout the day.

Example 3

1 g Triton RW-20 Alkylamine Ethoxylate, 0.24 g 30% $NaOCH_3$ in methanol, 0.01 g Thymol Blue (supplied by Acros), and 30 ml ethanol were combined. The mixture was heated to a boil. The solvent was then removed by boiling off to obtain a total volume between 5 and 10 ml. Using a cotton ball, the resulting solution was applied to the surface of a polyethersulfone filter strip and air-dried. The result was a solid, reversible $CO_2$ detector that changed from blue to yellow upon exposure to 5% $CO_2$ concentration and reverted to blue upon re-exposure to ambient $CO_2$ concentrations. During the peak of functionality, the overall color change, based on change of hue, change of luminosity and speed of color change, was moderate (rated 7 on a scale of 1 to 10). The rate of substantially complete change of color was on the order of 180 one-way changes/minute. The detector was not highly humidity resistant, remaining functional for less than a half hour at 100% humidity, gradually becoming non-functional over that time. When exposed to water, the dye washed off the detector.

Based on a 10 ml solution, the detector solution composition by weight %:

Thymol Blue Free Acid: 0.1%

Triton RW-20: 10%

$NaOCH_3$: 0.7%

Ethanol/Methanol: 89.2%

Example 4

A formulation was prepared using 0.3 g 20 wt % TDA-1 Tris[2-(2-methoxyethoxy)ethyl]amine in methanol, 0.6 g 50 wt % TDA-15 polyoxyethylene (15) tridecyl alcohol in methanol, 0.2 g 1 wt % Thymol blue (supplied by Sigma Aldrich) in methanol and methanol. pH adjustment was attempted with 1M $NaOCH_3$ in methanol over a wide variety of ranges however disks dipped in these formulations showed no response to $CO_2$ exposure. No functioning detectors were created.

Example 5

0.30 grams of 20 wt % methyltricaprylylammonium hydrogen sulfate (Aliquat® 128 HS, also called Aliquat® 134HS) in methanol, 0.60 grams of 50 wt % TDA-15 polyoxyethylene (15) tridecyl alcohol in methanol, 0.20 grams of 1 wt % Thymol blue (supplied by Sigma Aldrich) in methanol were combined. 0.2 grams of 1 M $NaOCH_3$ in methanol were added to give a blue solution. A polyethersulfone filter disk dipped in this solution resulted in a $CO_2$ detector which showed a rapid and reversible color change from blue to yellow upon exposure to 5% $CO_2$. The rate of substantially complete change of color exceeded 180 one-way changes/minute. The overall color change of the detector, based on change of hue, change of luminosity and speed of color change, was very good to excellent (rated 8-9 on a scale of 1 to 10). When a detector that had been stored for 2 days in a zip-loc bag was tested at 50% humidity on a fixture that cycled between ambient air (~0.03% $CO_2$) and 5% $CO_2$ at a rate of 12 cycles (24 changes in $CO_2$ concentration)/minute, the detector continued to cycle from blue to yellow and back for over 24 hours. When the humidity on the test fixture was raised to 98%, the detector changed color cycling from blue to yellow and back but ceased functioning after a few minutes, changing permanently to yellow. When a detector using this formula was exposed to ambient air, it would gradually (over 24 hours) change permanently to yellow. When a detector using this formula, sealed from air, was exposed to elevated temperatures (70° C.) for 6 days, it would gradually and permanently change to yellow.

Detector solution composition by weight %:

Quaternary ammonium compound: 4.6%

TDA-15: 23.1%

Thymol blue: 0.15%

$NaOCH_3$: 1.0%

Methanol: 71.2%

Example 6

0.30 grams of 20 wt % methyltricaprylylammonium hydrogen sulfate in methanol, 0.60 grams of 50 wt % Polyethylene glycol 8000 in methanol, 0.20 grams of 0.5 wt % Thymol blue (supplied by Sigma Aldrich) in methanol and methanol were combined. 0.2 grams of 1 M $NaOCH_3$ in methanol were added to give a blue solution. A polyethersulfone filter disk dipped in this solution resulted in a $CO_2$ detector which showed a rapid and reversible color change from blue-green to yellow upon exposure to $CO_2$ which was slightly slower than the TDA-15 polyoxyethylene (15) tridecyl alcohol formulation from the previous example. The rate of substantially complete change of color was on the order of 180 one-way changes/minute. The overall color change of the detector, based on change of hue, change of luminosity, and speed of color change, was very good (rated 7-8 on a scale of 1 to 10). When a detector that had been stored for 2 days in a zip-loc bag was tested at 50% humidity on a fixture that cycled between ambient air (~0.03% $CO_2$) and 5% $CO_2$ at a rate of 12 cycles/minute, the detector continued rapid function for about 5 hours. At 22 hours, it had faded to yellow with blue-green splotches.

Detector solution composition by weight %:

Quaternary ammonium compound: 4.6%

TDA-15: 23.1%

Thymol blue: 0.08%

$NaOCH_3$: 0.11%

Methanol: 72.1%

Example 7

0.30 grams of 20 wt % methyltricaprylylammonium hydrogen sulfate in methanol, 0.60 grams of 50 wt % TDA-15 polyoxyethylene (15) tridecyl alcohol in methanol, and 0.10 grams of 1 wt % m-cresol purple (supplied by Sigma Aldrich) in methanol were combined. 5 wt % $NaOCH_3$ in methanol was added dropwise to give a purple solution. A polyethersulfone filter disk dipped in this solution resulted in a $CO_2$ detector which showed a rapid and reversible color change from purple to yellow-green upon exposure to 5% $CO_2$ which was slightly slower than the Thymol blue formulation from example 5 above. The rate of substantially complete change of color exceeded 180 one-way changes/minute. The overall color change of the detector, based on change of hue, change of luminosity, and speed of color change, was very good (rated 7-8 on a scale of 1 to 10). When a detector that had been stored for 10 days in a zip-loc bag was tested at 50% humidity on a fixture that cycled between ambient air (~0.03% $CO_2$) and 5% $CO_2$ at a rate of 12 cycles/minute, the detector functioned well initially but after 22 hours, the detector had faded to periwinkle with yellow areas. One year later, a stored strip still functioned successfully at a rate of at least 180 one-way color changes/minute.

Example 8

0.8 g TDA-15 polyoxyethylene (15) tridecyl alcohol, 0.13 g methyltricaprylylammonium hydrogen sulfate, and 0.75 g 1% Thymol Blue Free Acid (supplied by Acros) in methanol were added into a 5 ml volumetric flask. The flask was heated on a hotplate so that components melted and mixed. When cool, 0.065 g 25% $NaOCH_3$ in methanol was added dropwise to obtain a blue solution, then an additional 0.10 g 25% $NaOCH_3$ in methanol was added. Methanol was then added to the 5 ml mark and the contents shaken to mix. With a cotton ball, the solution was then applied to the top of a polyethersulfone filter strip and allowed to air dry for 1 hour. The result was a rapid functioning reversible $CO_2$ detector whose overall color change, based on change of hue, change of luminosity, and speed of color change, was excellent (rated 9 on a scale of 1 to 10). The rate of substantially complete change of color exceeded 180 one-way changes/minute. The detector persisted in functioning for more than 30 breath cycles at 100% humidity. A similar formulation was stable for at least 7 days stored in a zip-loc bag at 70° C.

Example 9

Into a 50 ml beaker was added 1.6 g of 2EH-5-Polyoxyethylene (5) 2 ethyl hexanol, 0.26 g Methyltricaprylylammonium hydrogen sulfate, and 1.5 g 1% Thymol Blue Free Acid (supplied by Acros) in methanol. The flask was heated on a hotplate so that components melted and mixed. When cool, 0.13 g 25% $NaOCH_3$ in methanol was added dropwise until a blue solution was obtained, then an additional 0.20 g 25% $NaOCH_3$ in methanol was added. 3.6 g Methanol was then added and the contents stirred with a spatula to mix. With a cotton ball, the solution was then applied to the top of a polyethersulfone filter strip and allowed to air dry for 1 hour. The result was a rapid functioning reversible $CO_2$ detector whose overall color change, based on change of hue, change of luminosity and speed of color change, was very good (rated 8 on a scale of 1 to 10). The rate of substantially complete change of color exceeded 180 one-way changes/minute. The detector was not highly humidity resistant, remaining functional for only about 10 minutes at 100% humidity.

Detector Solution composition by weight %:

Thymol Blue Free Acid: 0.26%

Quaternary ammonium compound: 3.6%

2EH-5 Polyoxyethylene (5) 2 ethyl hexanol: 22.1%

Methanol: 72.9%

$NaOCH_3$: 1.1%

Example 10

Into a 50 ml beaker was added 1.6 g of LA-4 polyoxyethylene (4) lauryl alcohol, 0.26 g Methyltricaprylylammonium hydrogen sulfate, and 1.5 g 1% Thymol Blue Free Acid (supplied by Acros) in methanol. The flask was heated on a hotplate so that components melted and mixed. When cool, 0.13 g 25% NaOCH$_3$ in methanol was added dropwise until a blue solution was obtained, then an additional 0.20 g 25% NaOCH$_3$ in methanol was added. 3.6 g Methanol was then added and the contents stirred with a spatula to mix. With a cotton ball, the solution was then applied to the top of a polyethersulfone filter strip and allowed to air dry for 1 hour. The result was a rapid functioning reversible CO$_2$ detector whose overall color change, based on change of hue, change of luminosity and speed of color change, was excellent (rated 9 on a scale of 1 to 10). The rate of substantially complete change of color exceeded 180 one-way changes/minute. The detector was not highly humidity resistant, remaining functional for only about 10 minutes at 100% humidity.

Detector solution composition by weight %:

Thymol Blue Free Acid: 0.26%

Quaternary ammonium compound: 3.6%

LA-4 polyoxyethylene (4) lauryl alcohol: 22.1%

Methanol: 72.9%

NaOCH$_3$: 1.1%

Example 11

0.85 g Methyltricaprylylammonium hydrogen sulfate, 0.007 g Thymol Blue (supplied by Acros), 3.3 g methanol, and 0.8 g TDA-3 polyoxyethylene (3) tridecyl alcohol were combined. 30% NaOCH$_3$ in methanol was added dropwise to obtain a blue solution and then 0.1 g additonal 30% NaOCH$_3$ in methanol was added. The combination was mixed, then centrifuged for 10 min. The liquid fraction was pipetted into a beaker for use as the detector solution. A small amount of the solution was then applied to the top of a polyethersulfone filter strip and allowed to air dry for 1 hour. The result was a rapid functioning reversible CO$_2$ detector whose overall color change, based on change of hue, change of luminosity and speed of color change, was very good (rated 8 on a scale of 1 to 10). The rate of substantially complete change of color exceeded 180 one-way changes/minute. The detector was not highly humidity resistant, remaining functional for about 15 minutes at 100% humidity.

Example 12

5 g Methyltricaprylylammonium hydrogen sulfate, 0.002 g m-cresol purple (supplied by Spectrum) and 20 ml methanol were combined. 30% NaOCH$_3$ in methanol was added dropwise until a purple solution was obtained. The combination was mixed, then centrifuged for 10 min. The liquid fraction was pipetted into a beaker. Methanol was added to the remaining precipitate in tubes, stirred and then centrifuged again. The liquid fraction was pipetted off and then combined with the initially removed liquid fraction. 0.84 g of this liquid was then combined with 0.0025 g m-cresol purple, 0.83 g Triton X-100 octylphenol ethoxylate, and 3.36 g methanol. The mixture was mixed well with a spatula. With a cotton ball, a small amount of the mixture was applied to the top of a polyethersulfone filter strip and allowed to air dry for 1 hour. The result was a rapid functioning reversible CO$_2$ detector whose overall color change, based on change of hue, change of luminosity and speed of color change, was very good (rated 8 on a scale of 1 to 10). The rate of substantially complete change of color exceeded 180 one-way changes/minute. The detector persisted in functioning for 1 hour at 100% humidity.

Detector solution composition by weight %:

m-cresol purple Sodium Salt: 0.05%

Methyltricaprylylammonium methoxide: 16.7%

Octylphenol ethoxylate: 16.5%

Methanol: 66.8%

Example 13

6 g CSA-3 polyoxyethylene (3) cetyl stearyl alcohol and 14 g TDA-3 polyoxyethylene (3) tridecyl alcohol were combined in a beaker. The mixture was heated to melt and mix, then cooled. In a separate beaker, 0.8 g Methyltricaprylylammonium hydrogen sulfate, 0.0025 g Thymol Blue (supplied by Acros), 3.3 g methanol, and 0.85 of the CSA-3 polyoxyethylene (3) cetyl stearyl alcohol/TDA-3 polyoxyethylene (3) tridecyl alcohol mixture were combined. 30% NaOCH$_3$ in methanol was added dropwise until a blue solution was obtained then 0.1 g additional 30% NaOCH$_3$ in methanol was added. The combination was mixed, then centrifuged for 10 min. The liquid fraction was pipetted into a beaker for use as the detector solution. A small amount of the solution was then applied to the top of a polyethersulfone filter strip and allowed to air dry for 1 hour. The result was a rapid functioning reversible CO$_2$ detector whose overall color change, based on change of hue, change of luminosity and speed of color change, was very good (rated 8 on a scale of 1 to 10). The rate of substantially complete change of color exceeded 180 one-way changes/minute. The detector was not humidity resistant, remaining functional for only about 5 minutes at 100% humidity.

Example 14

5 g Methyltricaprylylammonium hydrogen sulfate, 0.005 g Thymol Blue (supplied by Acros), and 20 ml methanol were combined. 30% NaOCH$_3$ in methanol was added dropwise to obtain a blue solution. The solution was mixed, then centrifuged for 10 min. The liquid was pipetted off into a beaker and the methanol was boiled off. 0.4259 g of this phase transfer agent solution, 0.0024 g Thymol Blue, sodium salt, 0.4347 g CSA-3-polyoxyethylene (3) cetyl stearyl alcohol, and 1.3468 g methanol were combined. Heated to melt, and mixed. A small amount of the composition was applied to the top of a polyethersulfone strip and allowed to air-dry for 1 hour. The result was a poorly functioning reversible CO$_2$ detector whose overall color change, based on change of hue, change of luminosity and speed of color change, was barely functional (rated 2 on a scale of 1 to 10).

Example 15

5 g Methyltricaprylylammonium chloride was added to 20 ml of 10% Sodium phenoxide trihydrate in water in a separatory funnel. The mixture was shaken for 1 min, then allowed to separate. The aqueous layer was removed. The remainder was washed with 10 to 20 ml water 3 more times, allowing separation and removal of water each time. The organic layer was then removed. This is the isolated Methyltricaprylylammonium phenoxide. Into a 5 ml volumetric flask was added 0.80 g 1% Thymol Blue Free Acid (supplied by Acros) in methanol then 0.21 g Methyltricaprylyl ammonium phenoxide. The contents were swirled well to mix. 0.59 g Triton X-15 Octylphenol ethoxylate was added, then methanol to the 5 ml mark. The contents were shaken to mix. With a cotton ball, a small amount of the mixture was applied to the top of a polyethersulfone filter strip and allowed to air dry for 1 hour. The result was a rapid functioning reversible $CO_2$ detector whose overall color change, based on change of hue, change of luminosity and speed of color change, was moderate (rated 7 on a scale of 1 to 10). The rate of substantially complete change of color exceeded 180 one-way changes/minute. The detector was humidity and water resistant, continuing to function for more than 24 hours at 100% humidity.

Detector solution composition by weight %:
Thymol Blue Free Acid: 0.20%
Quaternary ammonium compound: 4.2%
Triton X-15: 11.8%
Methanol: 83.8%

Example 16

2 g Sodium Phenoxide trihydrate was dissolved in 50 ml methanol (4% solution). 2.8 g Methyltricaprylylammonium hydrogen sulfate was added with stirring 5 minutes. 0.45 g aliquot of the mixture was removed to a small beaker. 0.45 g Triton X-15 Octylphenol ethoxylate (supplied by Sigma Aldrich), 0.005 g Thymol Blue Sodium Salt (supplied by Acros), and 1.45 g methanol were added. With a cotton ball, a small amount of the mixture was applied to the top of a polyethersulfone filter strip and allowed to air dry. Half of the detector was transferred to a beaker of deionized water and stirred for 10 min, then air dried again. The result was 2 rapid functioning reversible $CO_2$ detectors (one water-washed and one unwashed) whose overall color change, based on change of hue, change of luminosity and speed of color change, was excellent (rated 9 on a scale of 1 to 10). The rate of substantially complete change of color exceeded 180 one-way changes/minute for both detectors. The detectors were humidity and water resistant. Both water washed (and dried) and unwashed detectors were fully functional after 4 hours at 100% humidity. It was apparent that they would continue to function for a significantly longer time but the actual longevity of function was not tested.

Example 17

2.5 g Tetraoctylammonium hydrogen sulfate was added to 30 ml of 10% Sodium phenoxide trihydrate in methanol in a beaker with stirbar. The mixture was stirred vigorously for 1 hour and then transferred to a 60 ml separatory funnel. Water was added to the top, forcing product to separate. The lower water/methanol layer was removed. The organic layer was washed with 30 ml water 2 more times, allowing separation and removal of water each time. Then the organic layer was removed. This is the isolated Tetraoctylammonium phenoxide. Into a 5 ml volumetric flask was added 0.8 g 1% Thymol Blue Free Acid (supplied by Acros) in methanol and then 0.4 g Tetraoctylammonium phenoxide. The contents were swirled well to mix. 1.2 g Triton X-15 Octylphenol ethoxylate was added, then methanol to the 5 ml mark. The contents were shaken to mix. With a cotton ball, a small amount of the mixture was applied to the top of a polyethersulfone filter strip and allowed to air dry for 3 hours. The result was a rapid functioning reversible $CO_2$ detector whose overall color change, based on change of hue, change of luminosity and speed of color change, was moderate (rated 6 on a scale of 1 to 10). The rate of substantially complete change of color was at least 180 one-way changes/minute. The detector was humidity and water resistant, remaining functional for more than 24 hours at 100% humidity.

Detector solution composition by weight %:
Thymol Blue Free Acid: 0.16%
Quaternary ammonium compound: 8.0%
Triton X-15: 24.0%
Methanol: 67.8%

Example 18

0.30 grams of 20 wt % Tetrabutylammonium hydrogen sulfate in methanol, 0.60 grams of 50 wt % TDA-15 polyoxyethylene (15) tridecyl alcohol in methanol, 0.20 grams of 1 wt % Thymol blue (supplied by Sigma Aldrich) in methanol and methanol were combined. 0.2 grams of 1 molar $NaOCH_3$ in methanol were added to give a blue solution. A polyethersulfone filter disk dipped in this solution resulted in a $CO_2$ detector that showed a very rapid and reversible color change from blue-green to yellow upon exposure to $CO_2$. The rate of substantially complete change of color exceeded 180 one-way changes/minute. The overall color change of the detector, based on change of hue, change of luminosity and speed of color change, was very good (rated 7-8 on a scale of 1 to 10). When a detector that had been stored for 2 days in a zip-loc bag was tested at 50% humidity on a fixture that cycled between ambient air (~0.03% $CO_2$) and 5% $CO_2$ at a rate of 12 cycles/minute, the detector had a relatively short functional life, the color eventually fading to green over a 5 hour period.

Detector solution composition by weight %:
Quaternary ammonium compound: 4.6%
TDA-15: 23.1%
Thymol blue: 0.15%
$NaOCH_3$: 1.0%
Methanol: 71.2%

Example 19

0.30 grams of 20 wt % Methyltributylammonium hydrogen sulfate in methanol, 0.60 grams of 50 wt % TDA-15 polyoxyethylene (15) tridecyl alcohol in methanol, and 0.20 grams of 1 wt % Thymol blue (supplied by Sigma Aldrich) in methanol were combined. 0.2 grams of 1 M $NaOCH_3$ in methanol were added to give a blue solution. A polyethersulfone filter disk dipped in this solution resulted in a $CO_2$ detector that showed a very rapid and reversible color change from blue-green to yellow upon exposure to $CO_2$. The rate of substantially complete change of color exceeded 180 one-way changes/minute. The overall color change of the detector, based on change of hue, change of luminosity and speed of color change, was very good (rated 7-8 on a scale of 1 to 10). This formulation gave performance and longevity results similar to terabutylammonium hydrogen sulfate in the example above. When a detector that had been stored for 2 days in a zip-loc bag was tested at 50% humidity on a fixture that cycled between ambient air (~0.03% $CO_2$) and 5% $CO_2$ at a rate of 12 cycles/minute, the sample had a relatively short functional life, the color eventually fading to green over a 5 hour period and continuing to fade to yellow w/blue-green splotches by 22 hours.

Detector solution composition by weight %:

Quaternary ammonium compound: 4.6%

TDA-15: 23.1%

Thymol blue: 0.15%

NaOCH$_3$: 1.0%

Methanol: 71.2%

Example 20

0.30 grams of 20 wt % 18-crown-6 ether in methanol, 0.60 grams of 50 wt % TDA-15 polyoxyethylene (15) tridecyl alcohol in methanol, 0.20 grams of 1 wt % Thymol blue (supplied by Sigma Aldrich) in methanol, and methanol were combined. 0.1 M KOH (supplied by JT Baker) in H$_2$O was added dropwise to give a blue solution. A polyethersulfone filter disk dipped in this solution resulted in a CO$_2$ detector which showed a rapid and reversible color change from blue to yellow upon exposure to 5% CO$_2$. The rate of substantially complete change of color exceeded 180 one-way changes/minute. The overall color change of the detector, based on change of hue, change of luminosity and speed of color change, was very good to excellent (rated 8-9 on a scale of 1 to 10). A detector that had been stored for 7 days in a zip-loc bag had faded to green. When this detector was tested at 50% humidity on a fixture that cycled between ambient air (~0.03% CO$_2$) and 5% CO$_2$ at a rate of 12 cycles/minute, the detector functioned well initially, cycling from green to yellow and back, but by 24 hours the color change had degraded so that cycling was from half green/half yellow to yellow and back.

Example 21

0.30 grams of 20 wt % 18-crown-6 ether in methanol, 0.60 grams of 50 wt % TDA-15 polyoxyethylene (15) tridecyl alcohol in methanol, and 0.10 grams of 1 wt % m-cresol purple (supplied by Sigma Aldrich) in methanol were combined. 0.1 M KOH (supplied by JT Baker) in H$_2$O was added dropwise to give a purple solution. A polyethersulfone filter disk dipped in this solution resulted in a CO$_2$ detector which showed a rapid and reversible color change from purple to yellow-green upon exposure to 5% CO$_2$. The rate of substantially complete change of color was on the order of 180 one-way changes/minute. This detector was noticeably slower than the one prepared with Thymol blue in the previous example. The overall color change of the detector, based on change of hue, change of luminosity and speed of color change, was very good (rated 7-8 on a scale of 1 to 10). When a detector that had been stored for 10 days in a zip-loc bag was tested at 50% humidity on a fixture that cycled between ambient air (~0.03% CO$_2$) and 5% CO$_2$ at a rate of 12 cycles/minute, the detector remained functional for about 24 hours, gradually fading to green over that time.

Detector solution composition by weight %:

m-cresol purple: 0.07%

Crown Ether: 4.0%

Triton X-15: 20%

KOH: 0.19%

Methanol: 42.6%

Water: 33.1%

Example 22

0.0793 g 18-crown-6 ether, 0.0029 g Thymol Blue (supplied by Acros), 0.2976 g Triton X-15 Octylphenol ethoxylate, 0.0063 g 30% NaOCH$_3$ in methanol, and 0.7612 g methanol were combined. With a cotton ball, applied to the top of a polyethersulfone filter strip and air-dried. The result was a rapid functioning reversible CO$_2$ detector whose overall color change, based on change of hue, change of luminosity, and speed of color change, was excellent (rated 9 on a scale of 1 to 10). The rate of substantially complete change of color exceeded 180 one-way changes/minute. The detector was not humidity resistant, remaining functional for only about 5 minutes at 100% humidity. The dye turned olive green when the detector was exposed to water.

Detector solution composition by weight %:

Thymol Blue Sodium Salt: 0.25%

Crown Ether: 6.9%

Triton X-15: 25.9%

NaOCH$_3$: 0.17%

Methanol: 66.7%

Example 23

0.3 g of 20 wt % dibenzo 18-crown-6 ether in methanol, 0.6 g of 50 wt %, TDA-15 polyoxyethylene (15) tridecyl alcohol in methanol, 0.2 g of 1 wt % Thymol blue (supplied by Sigma Aldrich) in methanol, and 0.12 g of 1 M NaOCH$_3$ in methanol were combined. A polyethersulfone filter disk dipped in this solution resulted in a CO$_2$ detector that showed a rapid and reversible color change from yellow-green to yellow upon exposure to CO$_2$. The overall color change of the detector, based on change of hue, change of luminosity and speed of color change, was very good (rated 7-8 on a scale of 1 to 10). When a detector that had been stored for 2 days in a zip-loc bag was tested at 50% humidity on a fixture that cycled between ambient air (~0.03% CO$_2$) and 5% CO$_2$ at a rate of 12 cycles/minute, the detector functioned well initially but gradually faded to yellow with a barely detectable response after 45 minutes.

Detector solution composition by weight %:

Crown Ether: 4.9%

TDA-15: 24.6%

Thymol blue: 0.16%

NaOCH$_3$: 0.66%

Methanol: 69.7%

Example 24

0.3 g of 20 wt % dibenzo 18-crown-6 ether in methanol, 0.6 g of 50 wt % TDA-15 polyoxyethylene (15) tridecyl alcohol in methanol, 0.2 g of 1 wt % Thymol blue (supplied by Sigma Aldrich) in methanol, and 0.2 g of 1 M KOH (supplied by JT Baker) in H$_2$O were combined. A polyethersulfone filter disk dipped in this solution resulted in a CO$_2$ detector which showed a rapid and reversible color change from light blue to yellow upon exposure to 5% CO$_2$. The overall color change of the detector, based on change of hue, change of luminosity and speed of color change, was very good (rated 7-8 on a scale of 1 to 10). When a detector that had been stored for 7 days in a zip-loc bag was tested at 50% humidity on a fixture that cycled between ambient air (~0.03% CO$_2$) and 5% CO$_2$ at a rate of 12 cycles/minute, the detector alternated between green and yellow, continuing to function for about 24 hours. When exposed to ambient conditions, the detector faded to green after a few days but still exhibited rapid response to changed $CO_2$ concentration. Over a few more days of ambient exposure, the detector faded to yellow and became non-functional.

Example 25

0.3 g of 20 wt % dibenzo 18-crown-6 ether in methanol, 0.6 g of 50 wt % TDA-15 polyoxyethylene (15) tridecyl alcohol in methanol, 0.1 g of 1 wt % m-cresol purple (supplied by Sigma Aldrich) in methanol were combined. 0.1 M KOH (supplied by JT Baker) in $H_2O$ was added dropwise until a purple solution was obtained. A polyethersulfone filter disk dipped in this solution resulted in a $CO_2$ detector that exhibited a rapid and reversible color change from purple to yellow-green upon exposure to $CO_2$. The overall color change of the detector, based on change of hue, change of luminosity and speed of color change, was very good (rated 7-8 on a scale of 1 to 10). When a detector that had been stored for 10 days in a zip-loc bag was tested at 50% humidity on a fixture that cycled between ambient air (~0.03% $CO_2$) and 5% $CO_2$ at a rate of 12 cycles/minute, the detector cycled between medium bluish-purple and green and continued to function for nearly 24 hours. At 22 hours, detector had faded to periwinkle with yellow splotches.

Detector solution composition by weight %:

m-cresol purple: 0.09%

Crown Ether: 5.4%

TDA-15: 26.8%

KOH: 0.06%

Methanol: 57.0%

Water: 10.7%

Example 26

Mixed 0.2514 g Dibenzo 18-crown-6 ether, 0.0045 g Thymol Blue, sodium salt (supplied by Acros), 0.6600 g Triton X-15 Octylphenol ethoxylate, 0.0095 g 1M KOH (supplied by Fisher) in methanol, and 5.0024 g methanol. With a cotton ball, applied residue to the top of a polyethersulfone filter strip and air-dried. The result was a rapid functioning reversible $CO_2$ detector whose overall color change, based on change of hue, change of luminosity and speed of color change, was very good (rated 8 on a scale of 1 to 10). The rate of substantially complete change of color exceeded 180 one-way changes/minute. The detector was not humidity resistant, remaining functional for less than 5 minutes at 100% humidity. Turns yellow-green in $H_2O$.

Detector solution composition by weight %:

Thymol Blue Sodium Salt: 0.08%

Crown Ether: 4.2%

Triton X-15: 11.1%

KOH: 0.01%

Methanol: 84.5%

Example 27

In a 100 ml flask combined 0.069 g Thymol Blue (supplied by Acros), 0.1 g Dibenzo 18-crown-6 ether, 2 pellets (about 0.2 g) of KOH (supplied by Fisher), 1 ml 30% $NaOCH_3$ in methanol, and 50 ml $CH_2Cl_2$. Mixed by stirring and refluxed for 5 hours. Filtered and distilled off solvent until a dark green residue remained. Combined 0.015 g of this residue, 0.1 g Triton X-15 Octylphenol ethoxylate, and 0.9 g methanol and mixed. Added 40 ml water. A separation of insoluble material occurred. Captured some of the material by pipette and smeared on a polyethersulfone filter strip and dried at 70° C. The result was a rapid functioning reversible $CO_2$ detector whose overall color change, based on change of hue, change of luminosity and speed of color change, was moderate (rated 7 on a scale of 1 to 10). The rate of substantially complete change of color on the order of 180 one-way changes/minute. The detector was not highly humidity resistant, remaining functional for less than 15 minutes at 100% humidity. The strip was a lime green color on drying.

Example 28

0.016 g Thymol Blue (supplied by Acros), 0.05 g dibenzo 18-crown-6 ether, 0.037 g potassium tert-butoxide (KOC$(CH_3)_3$) and 30 ml ethanol are mixed by stirring. The volume was reduced to about 5 ml by boiling off solvent. When cool, about 2 ml was removed to make an initial detector. Added 1.1 g Triton X-15 Octylphenol ethoxylate and mixed. With a cotton ball, applied to the top of a polyethersulfone filter strip and air-dried. The result was a rapid functioning reversible $CO_2$ detector whose overall color change, based on change of hue, change of luminosity and speed of color change, was excellent (rated 9 on a scale of 1 to 10). The rate of substantially complete change of color exceeded 180 one-way changes/minute. The detector was not highly humidity resistant, remaining functional for less than 1 hour at 100% humidity. When exposed to water, the dye washed off the detector.

Example 29

0.4 g KOH (supplied by Fisher), 0.04 g $H_2O$, 50 ml toluene (supplied by Sigma Aldrich) were combined in a 100 ml flask with stirring for 10 min. Added 0.01 g dibenzo 18-crown 6 ether and stirred 10 min. Added 0.003 g Thymol Blue (supplied by Acros) and stirred 2 hours 20 min. Added 0.5 g Triton X-15 Octylphenol ethoxylate and stirred for 1 hour. Vacuum-filtered the mixture through a Whatman #1 filter cup. Vacuum-distilled off toluene at 25° C.-30° C. until about 2 ml remained. With a cotton ball, applied to the top of a polyethersulfone filter strip and air-dried. The result was a rapid-response reversible $CO_2$ detector whose overall color change, based on change of hue, change of luminosity and speed of color change, was moderate (rated 7 on a scale of 1 to 10). The rate of substantially complete change of color was on the order of 180 one-way changes/minute. The detector was not highly humidity resistant, remaining functional for less than a half hour at 100% humidity.

Example 30

0.016 g Thymol Blue (supplied by Acros), 0.05 g di(tert-butyl)dibenzo 18-crown-6 ether, 0.037 g potassium tert-butoxide (KOC$(CH_3)_3$) and 30 ml ethanol were mixed by stirring. The volume was reduced to about 5 ml by boiling off solvent. When cool, added 1.1 g Triton X-15 Octylphenol ethoxylate and mixed. With a cotton ball, a small amount of the mixture was applied to the top of a polyethersulfone filter strip and air-dried. The result was a rapid functioning reversible $CO_2$ detector whose overall color change, based on change of hue, change of luminosity and speed of color change, was very good (rated 8 on a scale of 1 to 10). The rate of substantially complete change of color exceeded 180 one-way changes/minute. The detector was not highly humidity resistant, remaining functional for less than 1 hour at 100% humidity. When exposed to water, the dye washed off the detector.

Example 31

0.4 g KOH (supplied by Fisher), 0.05 g $H_2O$, and 50 ml toluene (supplied by Sigma Aldrich) were combined in a 100 ml flask with stirring for 10 min. 0.01 g di(tert-butyl)dibenzo 18-crown-6 ether and 0.01 g Acros Thymol Blue were added and stirred for 3 hours. 0.5 g Triton X-15 Octylphenol ethoxylate was added and the mixture was stirred for 3 hours. Vacuum-distilled off toluene at 40° C. Removed a small quantity of residue with a pipette and transferred to a beaker using about 10 ml of hexane. 1 ml of this hexane solution was mixed with about 0.1 g of Brij 78 polyoxyethylene 21 stearyl ether in a beaker and heated on a hot plate such that the Brij 78 polyoxyethylene 21 stearyl ether mixes into solution. With a cotton ball, applied to the top of a polyethersulfone filter strip and air-dried. The result was a rapid functioning reversible $CO_2$ detector whose overall color change, based on change of hue, change of luminosity and speed of color change, was moderate (rated 7 on a scale of 1 to 10). The rate of substantially complete change of color was on the order of 180 one-way changes/minute. The detector was not highly humidity resistant, remaining functional for less than 1 hour at 100% humidity. When exposed to water, the dye washed off the detector.

Example 32

25 grams of a 20 wt % solution of methyltricaprylylammonium hydrogen sulfate in toluene (supplied by EM Science) were placed in a separatory funnel along with 50 milliliters of 1 M trisodium phosphate ($Na_3PO_4$) in $H_2O$. Toluene was chosen as the solvent due to its immiscibility with water and its ease of removal from the phase transfer agent. The mixture was shaken for two minutes, the phases allowed to separate and the lower aqueous layer drained away. A fresh 50 ml portion of $Na_3PO_4$ was added and the procedure repeated. The pH of the first phosphate solution dropped from 12.15 to 11.51 indicating extraction of an acidic component (likely the hydrogen sulfate anion) from the toluene solution. The pH of the second phosphate solution decreased to only 12.11 (from 12.15) indicating that most of the extractable acidic component was removed with the first solution. The phases were separated and the toluene solution, presumably now containing a mixture of methyltricaprylylammonium phosphate, methyltricaprylylammonium hydrogen phosphate, and methyltricaprylylammonium dihydrogen phosphate, was placed into a single-neck flask. The toluene was removed on a rotary evaporator using a water aspirator as the vacuum source and a water bath at approximately 70° C. The resulting viscous liquid (similar in appearance to the initial methyltricaprylylammonium hydrogen sulfate) was dissolved in methanol to yield a 20 wt % solution. When 0.3 g of this material was placed in formulation with 0.6 g 50 wt % polyethylene glycol 8000 in methanol and 0.2 g 1 wt % Thymol blue (supplied by Sigma Aldrich) in methanol, a blue solution formed without pH adjustment and the polyethersulfone filter disk prepared from the solution showed a rapid, reversible color change from blue to yellow. The rate of substantially complete change of color exceeded 180 one-way changes/minute. The overall color change of the detector, based on change of hue, change of luminosity and speed of color change, was very good (rated 8 on a scale of 1 to 10). The rate of color change was slightly slower than with the methyltricaprylylammonium methoxide formulation of Example 5 above.

Detector solution composition by weight %:

Quaternary ammonium compound: 5.5%

PEG 8000: 27.3%

Thymol blue: 0.18%

Methanol: 67%

We claim:

1. A rapidresponse reversible dry surface $CO_2$ detector comprising a solid support imbedded with a $CO_2$ detector composition, said $CO_2$ detector composition comprising a phase transfer agent, a pH sensitive color indicator, and an ethoxylated alcohol, said phase transfer agent being a quaternary ammonium phenoxide of the form

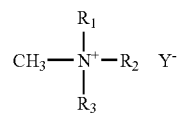

where:
$R_1$, $R_2$, and $R_3$, are alkyl or substituted alkyl groups each ranging from 8-12 carbons;
N is a nitrogen atom
$Y^-$ is a phenoxide or substituted phenoxide anion, said ethoxylated alcohol is an ethoxylated aliphatic alcohol or an ethoxylated phenol where the total number of carbons ranges from 12 to 54,
and said pH sensitive color indicator is sensitive to changes in pH between pH 7 and pH 11.

2. The rapidresponse reversible dry surface $CO_2$ detector according to claim 1 where said detector will repeatedly alternate between readily visibly distinguishable indicating colors in corresponding response to alternating exposure to ambient $CO_2$ concentrations and $CO_2$ concentrations of at least 2%.

3. The rapidresponse reversible dry surface $CO_2$ detector according to claim 2 where said detector changes from a first indicating color to a second readily visibly distinguishable indicating color in 0.33 seconds or less when exposed to $CO_2$ concentrations of at least 2% and substantially returns to the first indicating color in 0.33 seconds or less when reexposed to ambient air $CO_2$ concentrations.

4. The rapidresponse reversible dry surface $CO_2$ detector according to claim 1 where said phase transfer agent is methyltricaprylylammonium phenoxide, said pH sensitive color indicator is thymol blue and said ethoxylated alcohol is octylphenol ethoxylate.

5. The rapidresponse reversible dry surface $CO_2$ detector according to claim 4 where said $CO_2$ detector is substantially humidity resistant.

6. The rapidresponse reversible dry surface $CO_2$ detector according to claim 1 wherein said phase transfer agent is selected from the group consisting of methyltricaprylylammonium phenoxide, methyltrioctylammonium phenoxide, methyltridecylammonium phenoxide, methyldioctyldecylammonium phenoxide, methyldidecyloctylammonium phenoxide and any mixture of methyltrioctylammonium phenoxide, methyltridecylammonium phenoxide, methyldioctyldecylammonium, phenoxide and methyldidecyloctylammonium phenoxide.

7. The rapidresponse reversible dry surface $CO_2$ detector according to claim 1 where said ethoxylated alcohol is selected from the group consisting of octyiphenol ethoxylate, polyoxyethylene (3) tridecyl alcohol, polyoxyethylene (15) tridecyl alcohol, polyoxyethylene (5) 2 ethyl hexanol, polyoxyethylene (4) lauryl alcohol and polyoxyethylene (3) cetyl stearyl alcohol.

8. The rapidresponse reversible dry surface $CO_2$ detector according to claim 1 wherein the solid support is a polyethersulfone filter material.

9. The rapidresponse reversible dry surface $CO_2$ detector according to claim 1 located in an esophageal breathing system.

* * * * *